US 9,244,139 B2

(12) United States Patent
Brown et al.

(10) Patent No.: US 9,244,139 B2
(45) Date of Patent: Jan. 26, 2016

(54) METHOD AND APPARATUS FOR MRI COMPATIBLE COMMUNICATIONS

(71) Applicant: NeoCoil, LLC, Pewaukee, WI (US)

(72) Inventors: Brian Brown, Wauwatosa, WI (US); Manuel J. Ferrer Herrera, West Bend, WI (US)

(73) Assignee: Neocoil, LLC, Pewaukee, WI (US)

( * ) Notice: Subject to any disclaimer, the term of this patent is extended or adjusted under 35 U.S.C. 154(b) by 67 days.

(21) Appl. No.: 13/839,263

(22) Filed: Mar. 15, 2013

(65) Prior Publication Data

US 2014/0275970 A1    Sep. 18, 2014

Related U.S. Application Data

(60) Provisional application No. 61/648,876, filed on May 18, 2012.

(51) Int. Cl.
| | |
|---|---|
| *A61B 5/05* | (2006.01) |
| *G01R 33/36* | (2006.01) |
| *A61B 5/055* | (2006.01) |
| *G01R 33/28* | (2006.01) |
| *A61B 5/00* | (2006.01) |
| *A61B 5/1455* | (2006.01) |

(52) U.S. Cl.
CPC ............ *G01R 33/3692* (2013.01); *A61B 5/002* (2013.01); *A61B 5/0046* (2013.01); *A61B 5/055* (2013.01); *G01R 33/283* (2013.01); *A61B 5/14551* (2013.01)

(58) Field of Classification Search
CPC .... G01R 33/283; G01R 3/3692; A61B 5/055; A61B 5/002; A61B 5/14551; A61B 5/0046; A61N 1/3718

USPC .................................................. 600/407–480
See application file for complete search history.

(56) References Cited

U.S. PATENT DOCUMENTS

| | | | | |
|---|---|---|---|---|
| 5,313,945 | A * | 5/1994 | Friedlander | 600/410 |
| 6,463,316 | B1 * | 10/2002 | Brungart | 600/410 |
| 6,961,604 | B1 * | 11/2005 | Vahasalo et al. | 600/410 |
| 7,613,478 | B2 * | 11/2009 | Jabri et al. | 455/556.1 |
| 8,423,081 | B2 * | 4/2013 | Jabri et al. | 455/556.1 |
| 8,461,978 | B2 * | 6/2013 | Garner et al. | 340/539.1 |
| 2003/0013966 | A1 * | 1/2003 | Barnes et al. | 600/446 |
| 2003/0206019 | A1 * | 11/2003 | Boskamp | 324/322 |
| 2005/0197565 | A1 * | 9/2005 | Yagi et al. | 600/418 |
| 2006/0206024 | A1 * | 9/2006 | Weeks et al. | 600/418 |
| 2006/0241392 | A1 * | 10/2006 | Feinstein et al. | 600/422 |
| 2008/0146277 | A1 * | 6/2008 | Anglin et al. | 455/556.1 |
| 2008/0200796 | A1 * | 8/2008 | Graham et al. | 600/411 |
| 2010/0160784 | A1 * | 6/2010 | Poland et al. | 600/453 |
| 2010/0160785 | A1 * | 6/2010 | Poland et al. | 600/459 |
| 2010/0160786 | A1 * | 6/2010 | Nordgren et al. | 600/459 |
| 2010/0168576 | A1 * | 7/2010 | Poland et al. | 600/443 |

(Continued)

*Primary Examiner* — Sanjay Cattungal
(74) *Attorney, Agent, or Firm* — Boyle Fredrickson, S.C.

(57) ABSTRACT

An MRI compatible communication system is disclosed. An interface module manages communications between devices within and external to the MRI scan room. The interface module also translates messages between varying wireless communication standards and protocols for retransmission to other devices. The communication system is configurable to transmit and/or receive data between physiological sensors, the MRI controller, patient monitoring devices, patient entertainment devices, and other computers. The interface module is configurable to be placed either in the control room or in the scan room.

20 Claims, 8 Drawing Sheets

(56) References Cited

U.S. PATENT DOCUMENTS

| | | | |
|---|---|---|---|
| 2010/0192141 A1* | 7/2010 | Fisher et al. | 717/168 |
| 2010/0277305 A1* | 11/2010 | Garner et al. | 340/539.1 |
| 2011/0084694 A1* | 4/2011 | Waffenschmidt et al. | 324/318 |
| 2011/0103491 A1* | 5/2011 | Saes et al. | 375/241 |
| 2013/0028153 A1* | 1/2013 | Kim et al. | 370/310 |
| 2013/0174205 A1* | 7/2013 | Jacobsen et al. | 725/81 |
| 2013/0311176 A1* | 11/2013 | Brown et al. | 704/233 |

* cited by examiner

METHOD AND APPARATUS FOR MRI COMPATIBLE COMMUNICATIONS

CROSS-REFERENCE TO RELATED APPLICATIONS

This application claims priority to U.S. provisional application Ser. No. 61/648,876, filed on May 18, 2012, the entire contents of which is incorporated herein by reference.

BACKGROUND OF THE INVENTION

The subject matter disclosed herein relates to a system for MRI compatible communications. More specifically, a system for communication between devices within or external to an MRI scan room is disclosed.

As is known to those skilled in the art, a magnetic resonance imaging (MRI) system alternately generates a strong magnetic field and then detects the faint nuclear magnetic resonance (NMR) signals given off by nuclei in the presence of the magnetic field. The NMR signals are received by antennas, also known as coils, and transmitted to the MRI scanner for reconstruction into an MRI image. In order to provide a clear image, it is desirable to minimize electromagnetic interference from outside sources.

As a result, MRI scanners are located within a shielded room, also known as the scan room. Referring to FIG. 1, an exemplary shielded room 10 containing an MRI scanner 12 is illustrated. The scan room 10 includes walls 13, or panels, which typically incorporate the RF shielding within the wall 13. A window 15 permits an operator to observe activity within the scan room 10 from an adjacent control room 11, typically connected via a door 17. The door 17 may similarly incorporate RF shielding within the solid portion of the door. The window 15 between the scan room 10 and the control room 11 and, if present, a window in the door 17 are covered in a conductive material such as a fine wire mesh or a thin gold foil to provide RF shielding on the window. The shielding is configured to prevent external RF signals that are in a spectrum that may interfere with the MRI scanner 12 from entering the scan room 10 and causing said interference.

It is further desirable to minimize electronic components contained within the scan room 10 to prevent undesirable radiated emissions being generated. Consequently, the controller 20 for the MRI scanner 12 is typically located in the adjacent control room 11. An operator interface including, for example, a monitor 22 or other display unit and an input device such as a keyboard 24 are connected to the controller 20. The controller 20 may be connected to the MRI scanner 12 by cabling extending, for example, under the floor of the scan room 10 or in a shielded conduit to the MRI scanner 12. A penetration panel 23 in the wall may also provide connections to cables 21 running from the controller 20 into the scan room 10. The penetration panel 23 may include connectors for cabling to other medical equipment present in the scan room 10. Corresponding connectors on the other side of the penetration panel 23 within the scan room 10 permit appropriately shielded cables to be connected and run to the scanner 12 or to other medical equipment. A table 16 supports the patient being scanned and typically includes a sliding platform 19 allowing the patient to be moved into and out of the bore 14 of the MRI scanner 12.

It is typically necessary to include some additional equipment within the scan room 10. This additional equipment may be used, for example, to monitor the patient, communicate with the patient, or provide entertainment to the patient during a scan. Patients often require monitoring, for example, of heart rate, respiration, or other physiological factors. Further, acquiring images may take an extended period of time. Because the MRI operator is in the adjacent room and the patient is within the bore 14 of the MRI scanner, it may be necessary to include patient monitoring equipment within the MRI scan room 10. It may also be necessary for the MRI operator to communicate with the patient during acquisition of an image. In addition, it may be desirable to provide a distraction for the patient, such as some form of entertainment, during longer scans. Additional equipment may, therefore, be provided for monitoring and/or for communication.

When providing these additional electronic devices in the scan room, consideration must be given both to emissions from the devices interfering with the MRI scanner and emissions from the MRI scanner interfering with the devices. Often the devices include multiple components. For example, a sensor is connected to an associated recording device, a video camera includes a video cable extending to a monitor in the control room, or a video display is connected to a video storage device, such as a DVD player or a computer. Each of these devices, as well as their associated cabling, requires appropriate shielding. If the device either sends data out of or receives data in to the scan room 10, the cabling may pass through the penetration panel 23. As the number of devices in the scan room increases, the various cabling may interfere with each other or with medical personnel interacting with the patient.

Thus, it would be desirable to provide a system to wirelessly communicate with physiological sensors, patient communication systems, and/or an entertainment system that can communicate outside the shielded room without interfering with and degrading the quality of the MRI images.

BRIEF DESCRIPTION OF THE INVENTION

The subject matter disclosed herein describes an MRI compatible communication system. An interface module manages communications between devices within and external to the MRI scan room. The interface module also translates messages between varying wireless protocols for retransmission to other devices. The communication system is configurable to transmit and/or receive data between physiological sensors, the MRI controller, patient monitoring devices, patient entertainment devices, and other computers. The interface module is configurable to be placed either in the control room or in the scan room.

According to one embodiment of the invention, a communication system to permit communication between a patient undergoing a diagnostic imaging procedure and a technologist conducting the diagnostic imaging procedure is disclosed. The diagnostic imaging equipment includes a scanner configured to generate a diagnostic image and a controller configured to control operation of the scanner. The communication system includes an interface module, which, in turn includes an input connection configured to receive an audio signal from the controller, a wireless communication module configured to convert the audio signal to a radio frequency (RF) modulated signal having a frequency greater than a frequency of operation of the diagnostic scanner, and an output connection configured to conduct the RF modulated signal. An antenna is electrically connected to the output connection of the interface module and configured to transmit the RF modulated signal in proximity to the scanner, and at least one wireless receiver is configured to be positioned in proximity to the scanner and to receive the RF modulated signal.

According to another aspect of the invention, a supplemental audio source supplies a second audio signal, and the controller includes an electronic circuit configured to combine the second audio signal with the audio signal from the controller to generate a combined audio signal, and the combined audio signal is received at the input connection of the interface module. The interface module also includes an electronic circuit configured to separate the audio signal from the controller and the second audio signal out of the combined audio signal and a second output connection configured to conduct the audio signal from the controller, where either the audio signal from the controller or the second audio signal is converted to the RF modulated signal.

According to another embodiment of the invention, a supplemental audio source supplies a second audio signal and the controller includes an electronic circuit configured to combine the second audio signal with the audio signal from the controller to generate a combined audio signal. The communication system includes a second interface module, which, in turn, includes an input connection configured to receive the combined audio signal from the controller, an electronic circuit configured to separate the audio signal from the controller and the second audio signal out of the combined audio signal, and an output connection configured to receive a cable including multiple conductors. The cable is connected between the output connection of the second interface module and the input connection of the interface module. The audio signal from the controller and the second audio signal are transmitted on different conductors of the cable, and the interface module further includes a second output connection configured to conduct the audio signal from the controller. At least one of the audio signal from the controller and the second audio signal is converted to the RF modulated signal.

According to yet another embodiment of the invention, a communication system for radio frequency (RF) communications between a plurality of devices located either within or proximate to a scan room housing a medical diagnostic scanner includes an interface module configured to communicate with a controller for the medical diagnostic scanner. The interface module includes a wireless communication module configured to transmit and receive at least one RF modulated signal with at least one of the devices located proximate to the medical diagnostic scanner, where the RF modulated signals have a frequency greater than a frequency of operation of the diagnostic scanner. An antenna is configured to exchange the RF modulated signals between the interface module and each of the devices located proximate to the medical diagnostic scanner. At least one of the devices may be a sensor configured to monitor a physiological parameter of a patient in the medical diagnostic scanner and to transmit an RF modulated signal to the interface module including data corresponding to the physiological parameter being monitored, where the RF modulated signals have a frequency greater than a frequency of operation of the diagnostic scanner.

According to other aspects of the invention, the sensor includes an accelerometer generating a signal corresponding to motion of the sensor, and the sensor is further configured to transmit an RF modulated signal to the interface module including the signal from the accelerometer. A portable computing device having low magnetic susceptibility may be included. The portable computing device includes a wireless communication module configured to receive the RF modulated signals from the sensor, a memory device configured to store the signals from the sensor, and a display configured to provide a visual indication of the signals from the sensor to an operator. The medical diagnostic scanner includes a physiological acquisition control (PAC) unit configured to control image acquisition on the medical diagnostic scanner via a gating signal, and the PAC unit is further configured to receive an RF modulated signal which includes the gating signal from the interface module. The portable computing device is further configured to execute a stored program to generate the gating signal for the PAC unit as a function of the signals received from the sensor and to transmit the gating signal to the PAC unit.

According to still another embodiment of the invention, a wireless communication system for use during a diagnostic imaging procedure to communicate between a control room, which includes a controller configured to control operation of a diagnostic scanner, and a scan room which contains the diagnostic scanner, includes at least one portable device configured to engage a patient in the diagnostic scanner during operation of the diagnostic scanner. The portable device includes a wireless communication module configured to transmit and receive radio frequency (RF) modulated signals, where the RF modulated signals have a frequency greater than a frequency of operation of the diagnostic scanner. A portable computing device includes a memory device configured to store data and a series of instructions, a processor configured to execute the series of instructions, and a wireless communication module configured to communicate with the portable device.

According to another aspect of the invention, each of the portable devices may be sensors configured to monitor a physiological parameter of the patient in the diagnostic scanner and to generate a signal corresponding to the physiological parameter being monitored. Each of the signals corresponding to the physiological parameter being monitored are converted to RF modulated signals and transmitted to the portable computing device. The diagnostic scanner may also include a physiological acquisition control (PAC) unit configured to control image acquisition on the diagnostic scanner via a gating signal. The processor on the portable device is configured to execute the series of instructions to generate the gating signal as a function of at least one of the RF modulated signals corresponding to the physiological parameter being received from the sensors, to convert the gating signal to an RF modulated signal, and to transmit the RF modulated signal corresponding to the gating signal to the PAC unit.

According to yet another aspect of the invention, the portable computing device is configured to retrieve a stored data file that includes either audio video data from the memory device and to transmit the stored data file as an audio signal or a video signal, respectively, to the controller. The controller is configured to combine the audio signal or the video signal with an intercom signal for transmission to the patient. The wireless communication system may also include an interface module having an input connection configured to receive the combined signal from the controller, an electronic circuit configured to separate the audio or the video signal from the intercom signal, a wireless communication module configured to convert at least one of the audio signal, the video signal, or the intercom signal to a radio frequency (RF) modulated signal having a frequency greater than a frequency of operation of the diagnostic scanner, an antenna configured to transmit the RF modulated signal in proximity to the scanner, and an output connection configured to conduct the intercom signal. At least one receiver is configured to be positioned in proximity to the scanner and to receive the RF modulated signal. The wireless receiver may be either a wireless headset or a wireless monitor.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which.

Figure 1:
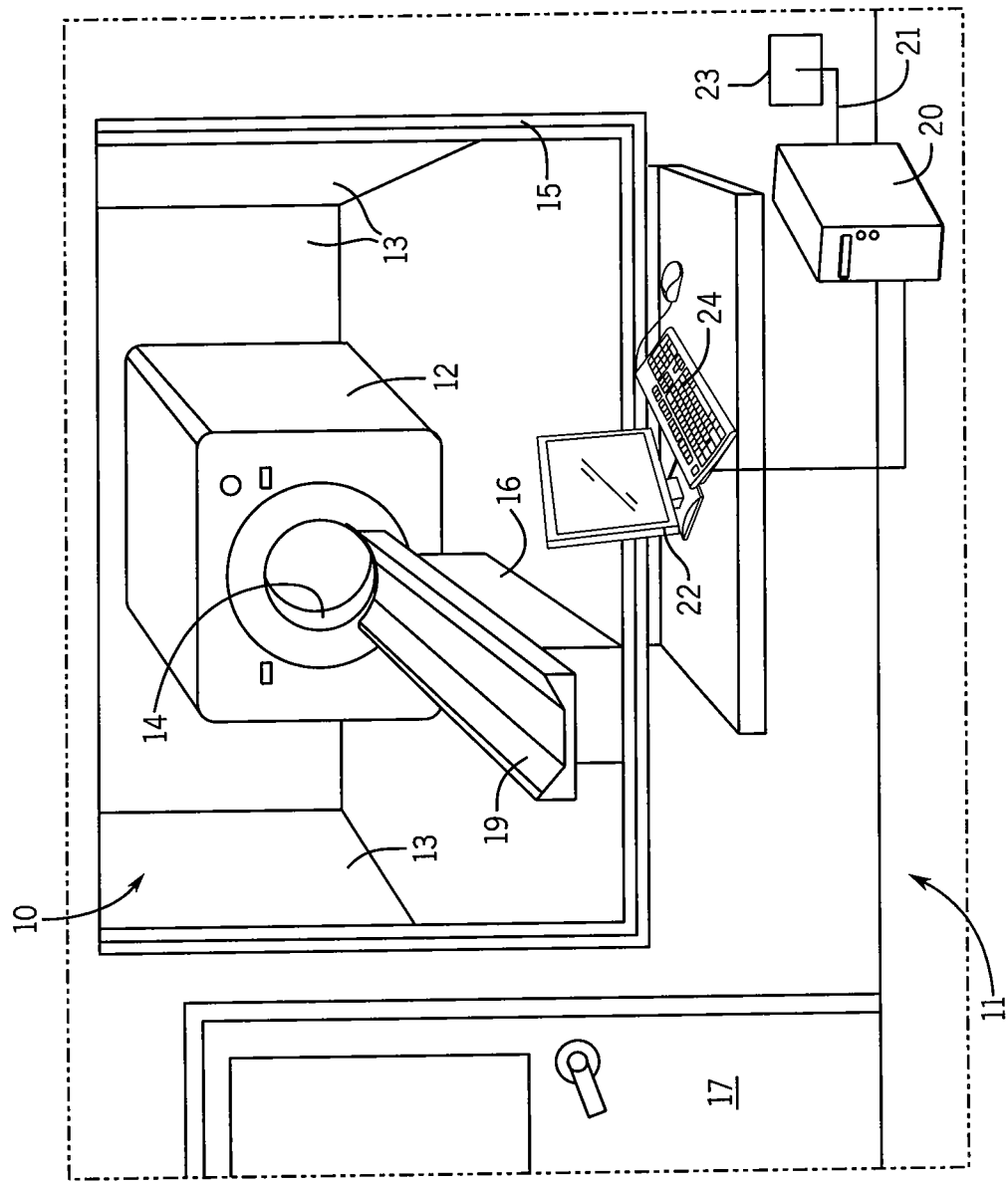
FIG. 1 is a exemplary embodiment of an existing MRI scan room.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Figure 2:
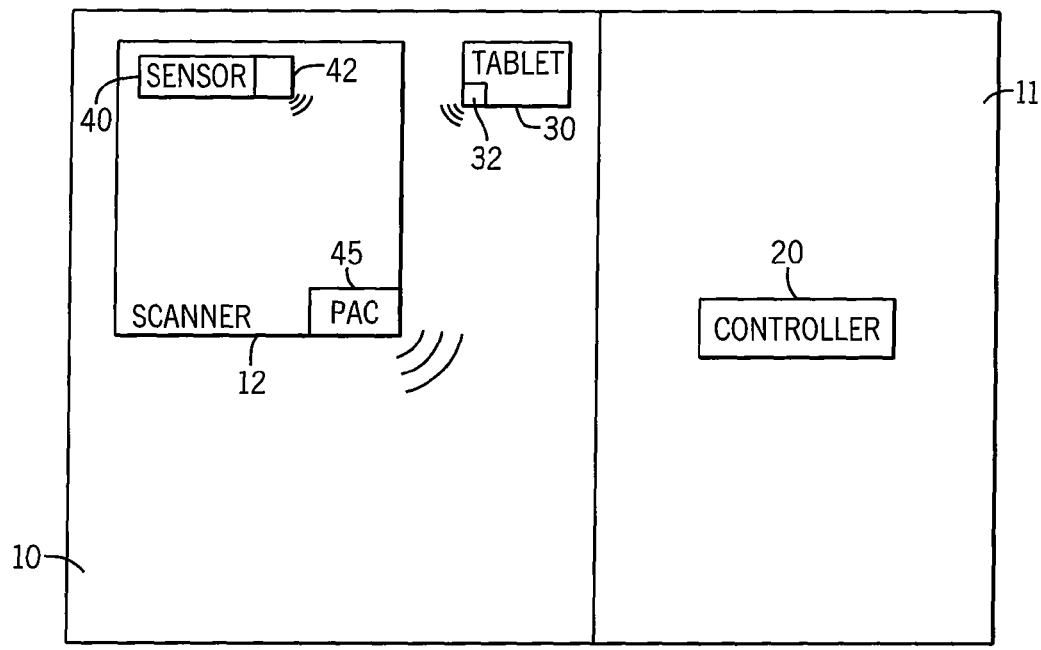
FIG. 2 is a block diagram representation of one embodiment of a communication system according to the present invention.

Referring initially to FIG. 2, an MRI compatible communication system includes a tablet computer 30 incorporating a wireless communication module 32. The tablet computer 30 executes a stored application to receive and/or transmit data via the wireless communication module 32 and provide a visual representation of the data on a display of the tablet computer 30. According to one embodiment of the invention, the wireless communication module 32 is configured to communicate using an appropriate communication standard, such as Bluetooth®. Optionally, the wireless communication module 32 may utilize any suitable communication standard. Data is received by an antenna connected to and typically integrated with the wireless communication module 32 from a remote device configured to communicate via the same standard. The data displayed on the tablet 30 may, for example, correspond to the operating status of the remote device or to data measured by the remote device.

The tablet 30 is configured to receive the data transmitted, for example, by a sensor 40. According to application requirements, the tablet 30 may store the data on a memory device and/or provide a visual representation of the data on a display device. The memory device may be volatile or non-volatile. Optionally, the tablet 30 may be removed from the scan room 10 and taken to a remote location where the stored data may be transmitted to another device, such as another computer, a monitor or other display device, or a printer. According to one embodiment of the invention, the tablet 30 is transferred to the control room 11 where the sensor data is transferred to the controller 20. The controller 20 may append the sensor data to an MRI image or to otherwise compensate an MRI image, for example, as a function of the patient's respiration during imaging. The tablet 30 is configured to not generate emissions, such as radiated electromagnetic interference (EMI) or radio frequency interference (RFI), that may interfere with the MRI scanner 12 and is further configured such that it does not include materials that are susceptible to being attracted by the magnetic field generated by the MRI scanner 12 (e.g. ferrous materials).

According to one embodiment of the invention, the remote device in communication with the wireless communication module 32 is a sensor 40 measuring a physiological parameter of a patient undergoing the MRI scan. The sensor 40 generates a signal corresponding to the physiological parameter measured, such as heart rate, blood oxygen level, or blood pressure. The electrical signal is provided to a wireless communication module 42 which is incorporated into the sensor 40 for transmission to a device, such as the tablet 30, external to the MRI scanner 12. The sensor 40 may also include an array of antennas (not shown), comprised of multiple individual antennas and mounted within the sensor 40. The array of antennas is arranged such that transmission may be optimized for a given direction or orientation. The sensor 40 may further include selection logic to enable/disable individual antennas such that the direction or orientation of transmission from the antenna array is selectable.

Additional features of the sensor 40 are configured to produce minimal interference with the MRI image. According to one embodiment of the invention, the sensor 40 is small in size to minimize potential distortion of an anatomical region being imaged. The sensor 40 may be positioned within the bore 14 of the MRI scanner 12 in a known orientation. An accelerometer (not shown) may also be mounted within the sensor 40. Preferably, the accelerometer detects a change in speed of the sensor in multiple axes (e.g. according to an x-y-z coordinate system). A processor within the sensor receives a signal from the accelerometer corresponding to the acceleration in each axis and determines the motion and resultant position of the sensor 40. The processor maintains a record of the relationship of the sensor 40 with respect to the MRI scanner 12 as a function of the original orientation of the sensor 40 within the MRI scanner 12 and the acceleration signals. The processor selectively enables a desired antenna for transmission as a function of the relationship of the sensor 40 to the MRI scanner 12. The acceleration signals may also be transmitted to the tablet 30 or to the controller 20 and used to track motion of the patient. Either a motion profile of the patient or the accelerometer signals directly, may be used in real-time or stored and used subsequently, to reduce artifacts introduced into an MRI image as a result of the patient's motion.

Figure 11:
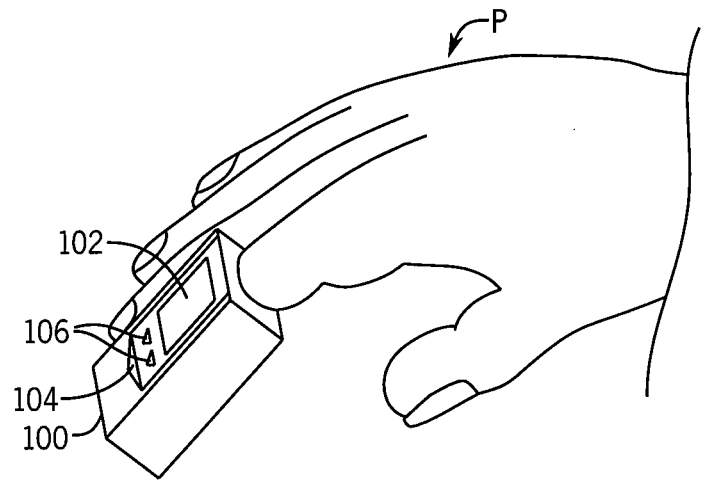
FIG. 11 is an exemplary sensor included in a communication system according to one embodiment of the present invention.
Figure 12:
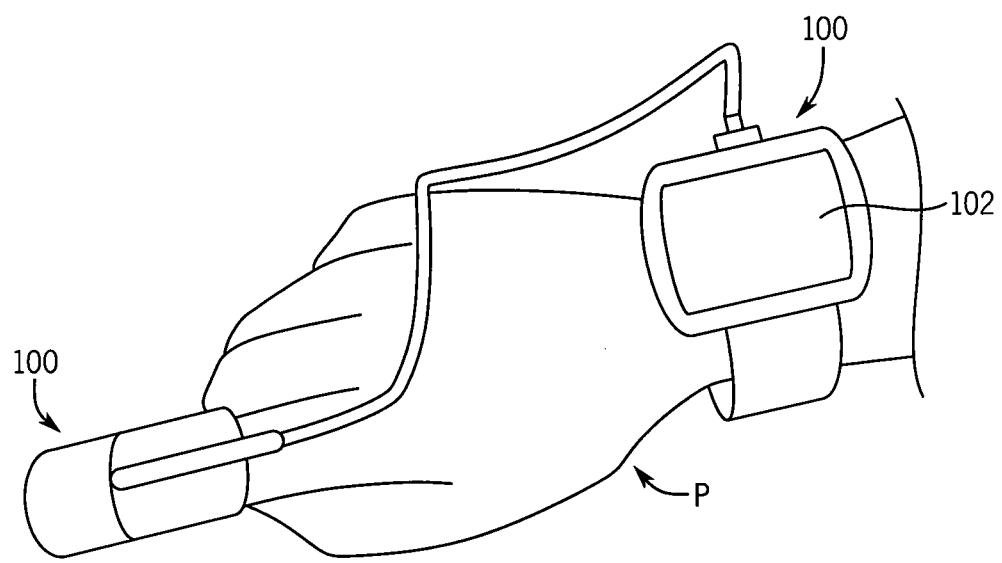
FIG. 12 is an exemplary sensor included in a communication system according to another embodiment of the present invention.

Referring also to FIG. 11, an exemplary pulse oximetry sensor 100 for use with the communication system is illustrated. The pulse oximetry sensor 100 includes a display unit 102 which may provide operation information, such as remaining battery life or strength of signal, or patient information, such as the oxygenation level of the patient's blood. A power indicator 104 may indicate that the sensor 100 is operating and one or more selection buttons 106 may be used to adjust operation of the sensor 100. Optionally, a pulse oximetry sensor 100 having no display may be used in order to minimize the size of the sensor 100 and, consequently, minimize artifacts introduced in an MRI scan from the sensor 100. Operation of the pulse oximetry sensor may be controlled remotely, for example, by transmitting a wake-up message to the sensor or via one or more selection buttons 106 on the sensor 100. The sensor 100 may include no visual indicators or may include, for example, light emitting diodes (LEDs) on the surface or a backlit panel where different combinations of LEDs, colors of LEDs or backlight, or illumination rates (e.g. blinking) may provide an indication of the operating status of the sensor 100.

It is further contemplated that the physiological acquisition control (PAC) unit 45 of the MRI scanner 12 may be configured for wireless communication. The PAC receives a gating signal used to coordinate timing between generating the magnetic field in the MRI scanner 12 and receiving and recording the NMR signals for generation of an MRI image. According to one embodiment of the invention, the gating signal is generated by the tablet 30 as a function of the physiological data received to coordinate imaging, for example, with the heart beat or respiration of the patient. The gating signal is then transmitted from the tablet 30 to the PAC unit 45. According to yet another embodiment of the invention, the gating signal is generated by the sensor 100 as a function of the physiological parameter being measured and transmitted by the sensor 100 to the PAC unit 45.

Figure 3:
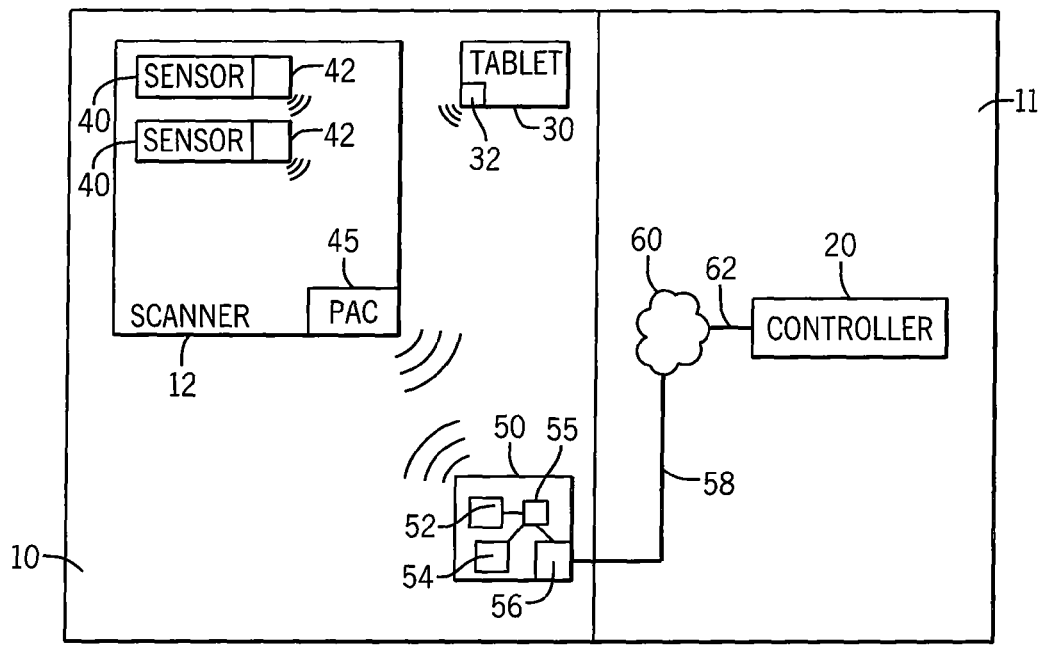
FIG. 3 is a block diagram representation of another embodiment of a communication system according to the present invention.

According to another embodiment of the invention, the communication system includes an interface module 50, shown in FIG. 3, configured to receive data wirelessly transmitted from one or more sensors 40 and configured to retransmit the data either wirelessly or via a wired connection to another device. The interface module 50 includes at least one wireless communication module, 52 or 54. A first wireless communication module 52 is configured to transmit and/or receive data using a Wi-Fi technology established, for example, by the IEEE 802.11 family of standards. A second communication module 54 is configured to transmit and/or receive data using a second wireless technology established, for example, by the Bluetooth® standard. Each wireless communication module 52, 54 transmits and/or receives communications via at least one antenna connected to and typically integrated with the wireless communication module 52, 54. Optionally, the interface module 50 also includes a network interface 56, providing a connection to a wired network 60, such as the Internet or an intranet, via any suitable network cable 58. As further illustrated in FIGS. 8 and 9, the interface module 50 may include an electronic circuit 57 configured according to application requirements to interface with other inputs, such as proprietary cabling extending between a controller 20 and a scanner 12.

The network cable 58 may pass through an opening between the scan room 10 and the control room 11. The opening being formed, for example, in the wall or existing around a door 17 providing access to the scan room 10. According to another embodiment, a pair of connectors on either side of the penetration panel 23 may be added for the network cable 58. According to still another embodiment, the interface module 50 may also be configured to communicate wirelessly between the scan room 10 and the control room 11. For example, the wired network 60 may include a wireless access point located in the control room 11 to which the interface module 50 may communicate, eliminating the need for a network cable 58 passing between the scan room 10 and the control room 11. The wired network 60 may be a local area network (LAN), including one or more additional network devices, including but not limited to a router, switch, or repeater. The controller 20 may also be connected to the network 60 via a network cable 62 for communication with the interface module 50. The network may utilize any standard networking technology such as Ethernet or a proprietary networking technology according to application requirements. Each of the wireless communication modules 52, 54 and the network interface 56 communicate with a processor 55. It is contemplated that the processor 55 may be a single device or multiple devices executing in parallel. The processor 55 may be a microprocessor, a microcontroller, a field programmable gate array (FPGA), an application specific integrated circuit (ASIC), or any combination thereof.

Figure 4:
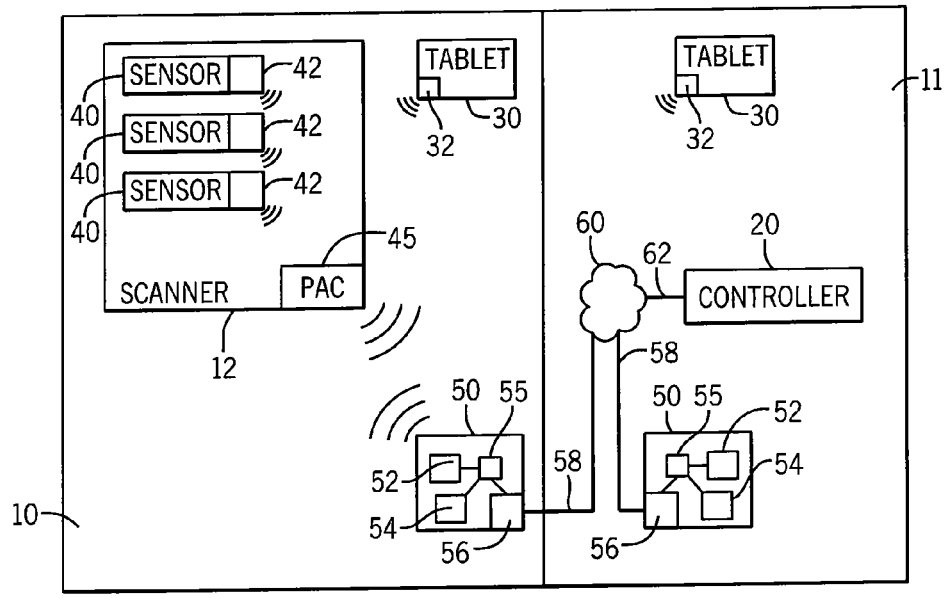
FIG. 4 is a block diagram representation of another embodiment of a communication system according to the present invention.

Referring next to FIG. 4, still another embodiment of a communication system according to the present invention is illustrated. A first interface module 50 is located within the scan room 10 and connected via a first network cable 58 to the LAN 60. A second interface module 50 is located in the control room 11 and connected via a second network cable 58 to the LAN 60. It is further contemplated that the connection between the first and second interface modules 50 may be made directly via a single network cable 58 passing through either an opening or the penetration panel 23 between the scan room 10 and the control room 11. The opening being formed, for example, in the wall or existing around a door 17 providing access to the scan room 10. It is further contemplated that the interface modules 50 may communicate directly via wireless communications and one or both of the interface modules 50 may communicate with a wireless access point connected to the LAN 60. Although illustrated as two tablets 30, a single tablet 30 may be moved between the scan room 10 and the control room 11, communicating with the respective interface module 50. Optionally, the controller 20 may include a wireless communication module and be configured to communicate wirelessly to an interface module 50.

Figure 5:
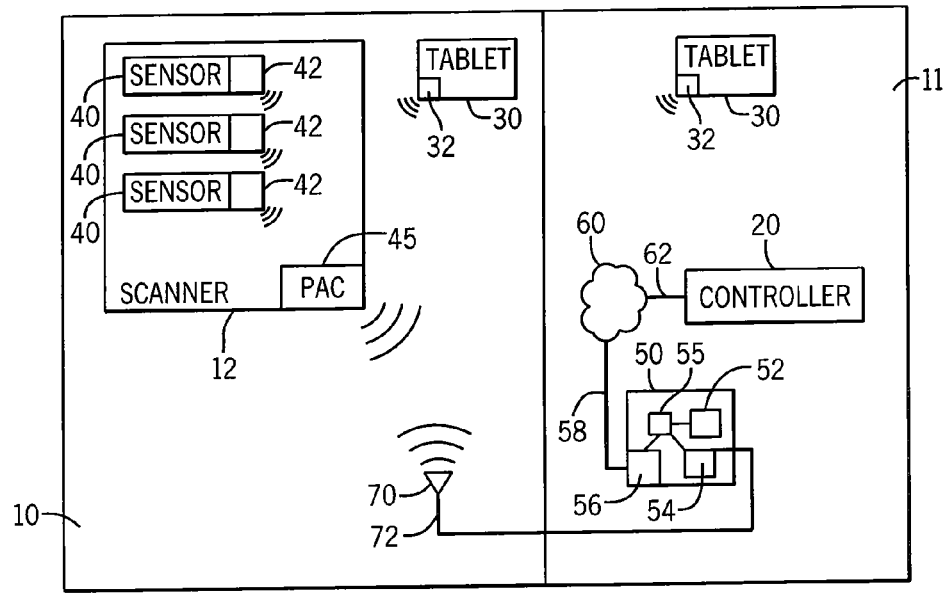
FIG. 5 is a block diagram representation of another embodiment of a communication system according to the present invention.
Figure 6:
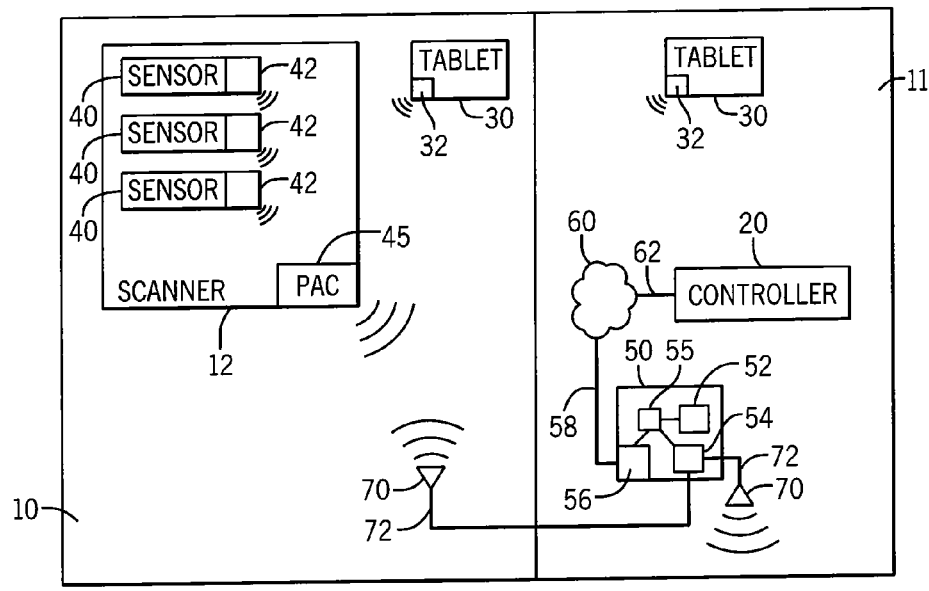
FIG. 6 is a block diagram representation of another embodiment of a communication system according to the present invention.
Figure 7:
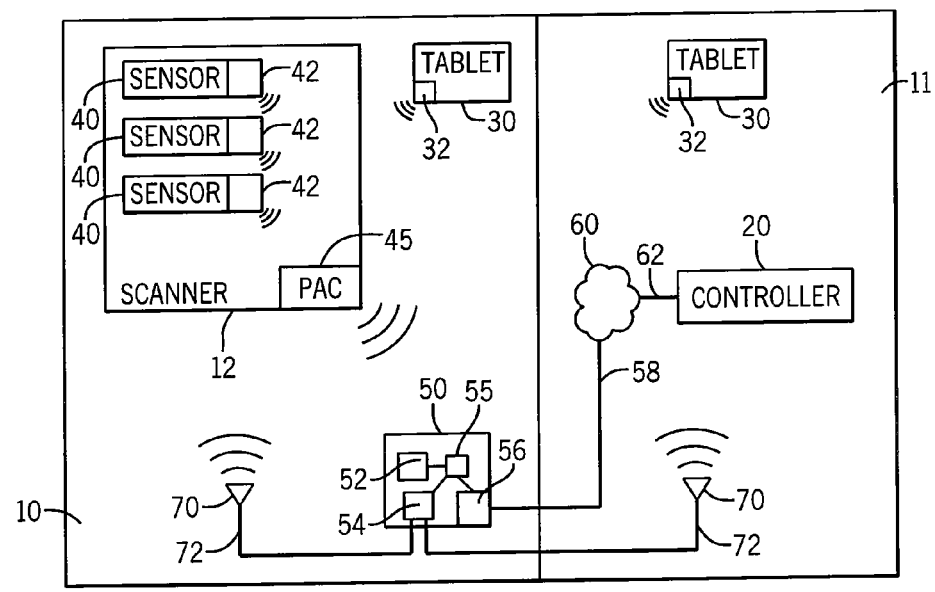
FIG. 7 is a block diagram representation of another embodiment of a communication system according to the present invention.

Referring next to FIG. 5, still another embodiment of the communication system according to the present invention is illustrated. An interface module 50 is located in the control room 11 and a first antenna 70 is positioned remote from the interface module 50 within the scan room 10. The antenna 70 may be configured to transmit and/or receive messages according to multiple wireless communication standards simultaneously (e.g. Wi-Fi or Bluetooth®). An antenna cable 72 is connected between the remote antenna 70 and the respective wireless communication module 52, 54. The antenna cable 72 is a shielded coaxial cable passing through either an opening or the penetration panel 23 between the scan room 10 and the control room 11. The opening being formed, for example, in the wall or existing around a door 17 providing access to the scan room 10. Referring also to FIG. 6, a second antenna 70 may be connected to the interface module 50. The second antenna 70 may be configured to transmit and/or receive messages via a single wireless communication standard (e.g. Wi-Fi). Optionally, the interface module 50 may be located in the scan room 10, as shown in FIG. 7. A first antenna 70 located within the scan room 10 may again be configured to communicate via multiple wireless communication standards and a second antenna 70 positioned within the control room 11 may be configured to communicate via a single wireless standard. In any of the embodiments illustrated in FIGS. 5-7, a single interface module 50 may provide wireless communications in both the scan room 10 and the control room 11. Optionally, the interface module 50 may communicate wirelessly with an access point connected to the LAN 60, eliminating the network cable 58. Still other combinations and arrangements of interface modules 50, antennas 70 and other wireless devices are contemplated without deviating from the scope of the present invention.

Figure 8:
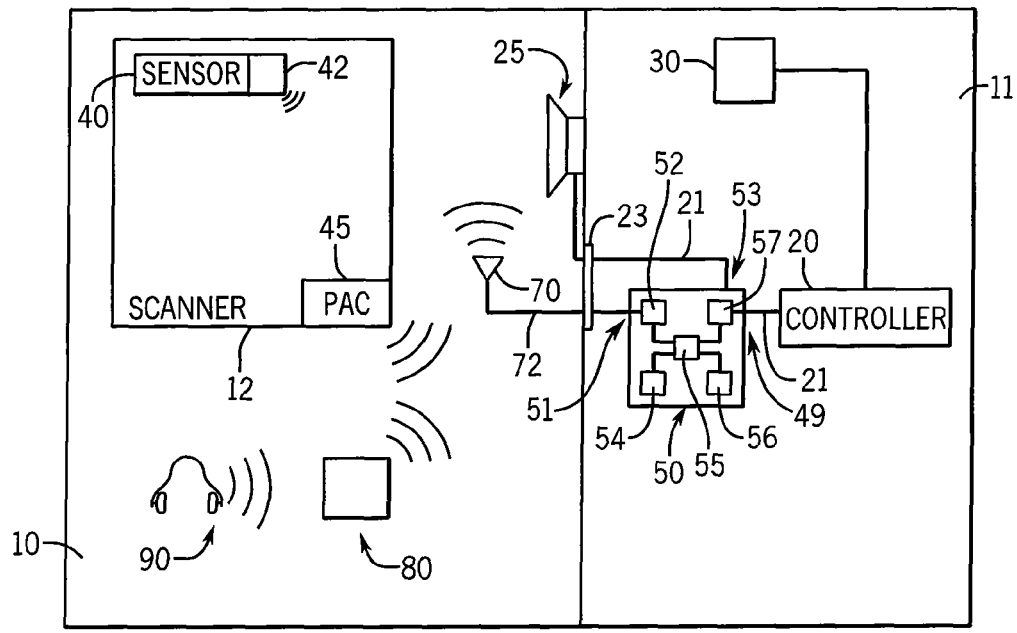
FIG. 8 is a block diagram representation of another embodiment of a communication system according to the present invention.

Referring next to FIG. 8, the interface module 50 may be configured to receive a cable 21 from the controller 20. The cable 21 is configured to carry one or more signals from the controller 20 into the scan room 10. One of the signals may be an audio signal used for communication with the patient. An intercom system including a microphone, provided in the control room 11, generates the audio signal corresponding to instructions and/or information spoken by the MRI technologist. Typically, the cable 21 may extend from the controller 20 through the penetration panel 23 and be connected to a speaker 25 mounted within the scan room 10. In the illustrated embodiment, the cable 21 is connected to an input connection 49 of the interface module 50. An electronic circuit 57 in the interface module 50 routes the signals from the input connection 49 to an output connection 53, to the processor 55, or to a wireless communication module 52 or 54. It is contemplated that the electronic circuit 57 may execute separately from the processor 55 or, optionally, may be integrated into the processor 55. The wireless communication module 52 or 54 converts the audio signal into a modulated RF signal for transmission over the antenna 70. The modulated RF signal is conducted to the antenna 70 via the antenna cable 72 connected between an output connection 51 and the antenna 70. A wireless headset 90 includes a receiver configured to receive the modulated RF signal and to reproduce the audio signal for distribution to the patient.

It is further contemplated that a supplemental audio source may be provided, for example, to provide music to a patient during a lengthy procedure. The supplemental audio source may be the tablet 30 or any other suitable portable electronic device configured to store digital music files. Optionally, a compact disc player or any other suitable media player may be provided to provide an audio signal from suitable medium. The controller 20 may be configured to receive the second audio signal and combine it with the intercom signal. The two audio signals may be, for example, multiplexed onto a single cable using, for example, frequency-division multiplexing, time-division multiplexing, or any other suitable multiplexing method as is understood in the art. The combined audio signal is then transmit to the interface module 50. The electronic circuit 57 and/or the processor 55 are configured to separate the two audio signals through an inverse procedure of that performed to combine the signals. The first audio signal, (e.g., the intercom signal) is transmitted to a speaker 25, if present, via an output connection 53 from the interface module 50. The wireless communication module 52 or 54 may convert the first audio signal, the second audio signal, or both audio signals into modulate RF signals for transmission via the antenna 70.

Figure 9:
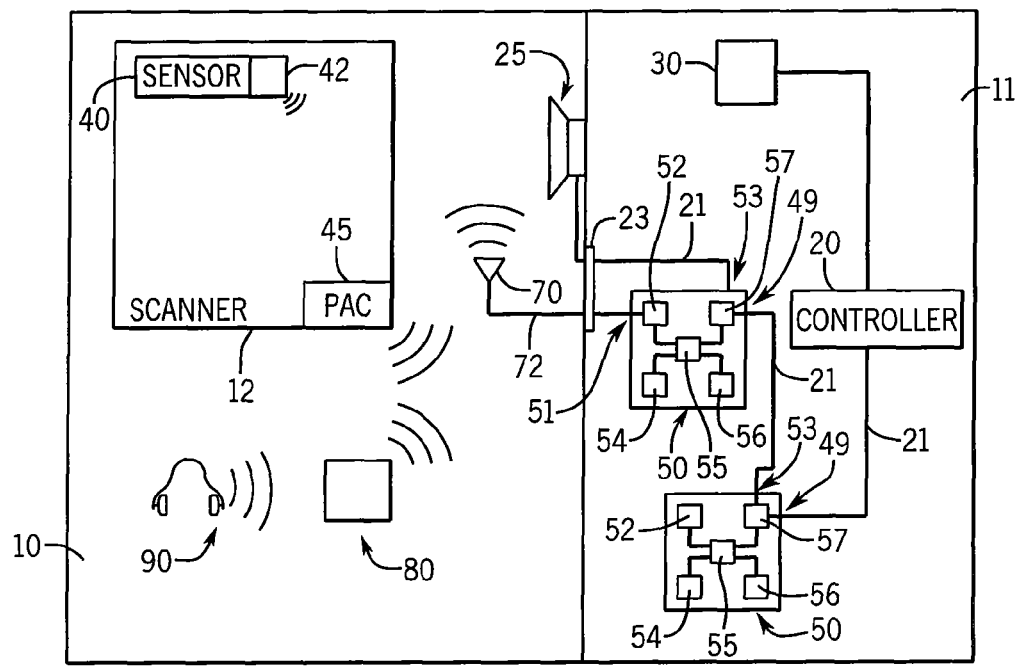
FIG. 9 is a block diagram representation of another embodiment of a communication system according to the present invention.

Referring next to FIG. 9, it is further contemplated that a second interface module 50 may be provided. The two interface modules 50 work in cooperation to transmit the first and second audio signals to the patient. The combined audio signal is provided via the cable 21 to the input connection 49 of the second interface module 50. The electronic circuit 57 and/or processor 55 of the second interface module 50 is configured to separate the two audio signals through an inverse procedure of that performed to combine the signals. Another length of cable 21 is provided between an output connection 53 of the second interface module 50 and the input connection 49 of the first interface module 50. The two audio signals may be transmitted as separate signals over different conductors, or pairs of conductors, within the cable 21. The second interface module 50 receives each of the two audio signals. The first audio signal, (e.g., the intercom signal) is transmitted to a speaker 25, if present, via an output connection 53 from the interface module 50. The wireless communication module 52 or 54 may convert the first audio signal, the second audio signal, or both audio signals into modulate RF signals for transmission via the antenna 70.

Figure 10:
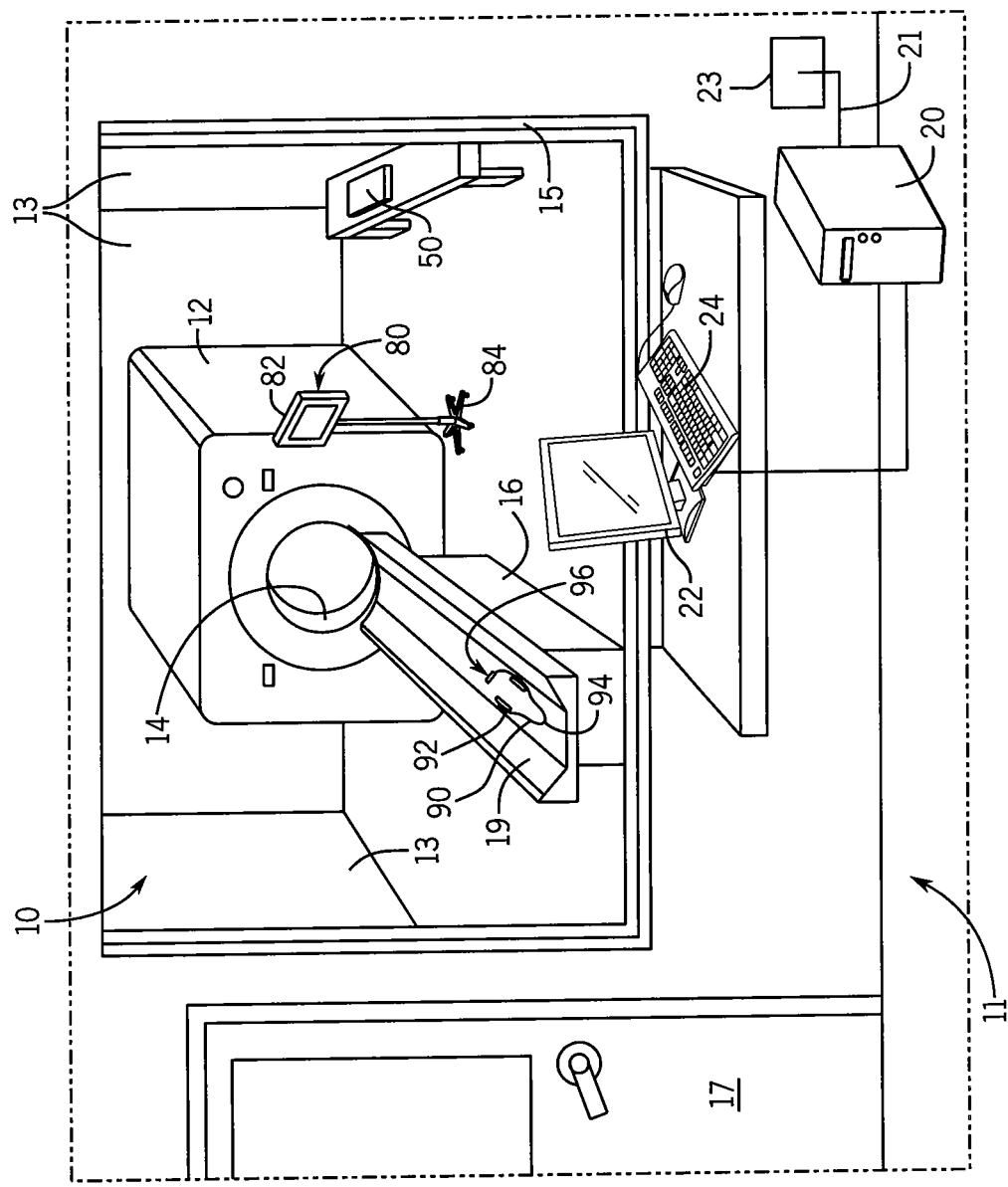
FIG. 10 is an exemplary embodiment of the MRI scan room of FIG. 1, incorporating a communication system according to one embodiment of the present invention.
Figure 13:
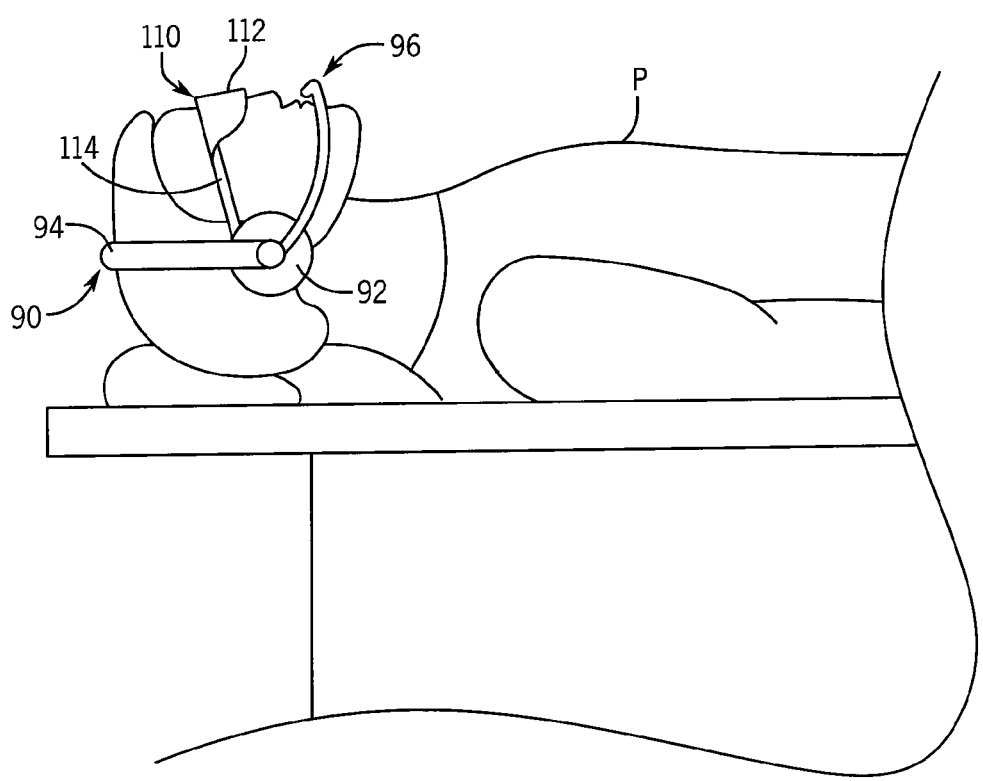
FIG. 13 is an exemplary embodiment of wireless communication devices providing two-way communications with a patient according to one embodiment of the present invention.

According to another embodiment of the invention, the wireless communication system may be configured to communicate with and/or to provide entertainment options to the patient. Referring to FIG. 10, a wireless headset 90 and/or a wireless video display module 80 may communicate with the interface module 50. As illustrated, the wireless headset 90 includes a pair of ear phones 92 joined by a head band 94. Optionally, a microphone 96 may be mounted on the headset 90. It is contemplated that numerous other configurations of the headset 90 as known in the art may be used without deviating from the scope of the invention. The display module 80 includes a monitor 82 for displaying the video information and a stand 84 to support the monitor 82. Preferably the stand is easily positioned within the scan room 10 to facilitate viewing by the patient being scanned. Referring also to FIG. 13, video information may also be provided to the patient, P, via a wireless viewing device 110 that may be worn much like a pair of glasses. The wireless viewing device 110 may include a pair of stems 114 which fit behind the patient's ears and a viewing screen 112 that is positioned in front of the patient's eyes. The wireless viewing device 110 allows a patient to receive visual information even when the patient's head is located within the bore of the MRI scanner or in a position not suited to view another display module 80.

In operation, the communication system provides wireless communication between devices inside and external to the scan room 10 with little or no interference to the quality of the MRI image. MRI scanners typically operate at frequencies in the range of 1 MHz to 100 MHz. Therefore, wireless communication modules for each of the devices in the system are selected that communicate at RF frequencies substantially greater than these operating frequencies, for example 2.4 GHz or 5.8 GHz.

Physiological sensors 40 are further configured to minimize interference with the image quality. The sensors 40 are constructed of non-ferrous materials such that they are not affected by the magnetic fields generated by the MRI scanner. Further, the electronic signals within the sensor 40 and the wireless transmission of data may similarly influence the MRI imaging process. As a result, the sensor 40 may include electromagnetic shielding within its housing. The shielding preferably minimizes electromagnetic radiation generated by electronic signals within the sensor while permitting the wireless transmission of data to pass through. Optionally, an antenna or antenna array may be positioned between the shielding and the housing of the sensor 40 or external to the housing. An electrical conductor is connected to the antenna or antenna array and passes through the shielding to a processing device to transfer data from the processing device to the antenna for subsequent transmission to a remote device.

If an antenna array is included within the sensor 40, the processing device may select one or more of the antennas to transmit data in a manner that reduces interference with the MRI imaging. For example, individual antennas may be enabled/disabled such that transmission may be optimized for a given direction or orientation. Optionally, the processing device may cause the relative phase or signal amplitude of the data being transmitted to vary for different antennas in order to achieve a desired overall radiation pattern. An initial orientation of the sensor 40 may be determined. For example, an MRI technologist or other medical personnel may place the sensor 40 in a predetermined orientation and provide an input, such as a pushbutton, to the sensor 40. The input is received by and indicates to the processing device that the sensor is in the preset position. It is contemplated that other methods of orienting the sensor 40 may be utilized without deviating from the scope of the invention. Subsequently, the processing device receives at least one input signal from the accelerometer corresponding to changes in motion of the sensor 40. The processing device may convert the accelerometer signals to a velocity and/or a position along the accelerometer axis to maintain knowledge of the orientation of the sensor 40 with respect to the preset position. According to one embodiment of the invention, the accelerometer provides signals along each of an x-axis, a y-axis, and a z-axis such that a three dimensional orientation of the sensor 40 is known. The processing device may subsequently select one or more antennas from the antenna array to transmit in a desired direction. The desired direction may be selected for example as a function of the orientation of the sensor 40 with respect to the magnetic fields being generated by the MRI scanner 12 such that the wireless communications produce minimal interference with the imaging process. Optionally, the desired direction may be selected to provide the strongest signal available from the sensor 40 to the interface module 50.

The wireless sensor 40 transmits data corresponding to a measured physiological parameter via its wireless communication module 42. For example, the sensor may measure the heart rate, oxygen level in the blood, or blood pressure. According to one embodiment of the invention, the data is received directly by a tablet computer 30 via its respective wireless communication module 32. The tablet 30 may store the data, for example, on a hard drive and/or provide a visual representation of the data on its monitor. The visual representation may be a real-time display, such as a number or bar graph, indicating the present value or a historical display such as a strip chart.

According to another embodiment of the invention, the interface module 50 provides a connectivity hub to devices both inside and external to the scan room 10 and receives the wireless communications from the sensor 40. The interface module 50 is configured to receive multiple wireless communications in tandem. The second communication module 54 is configured to simultaneously receive multiple signals according to the Bluetooth® standard. According to one embodiment of the invention, up to seven signals may be read at the same time. Each of the signals may be transmitted, for example, by different physiological sensors, a wireless communication or patient monitoring system, a wireless patient entertainment system, or a combination thereof. The processor 55 executes a series of stored instructions to read the data from each of the messages. One or more modules may be executing on the processor 55 to convert the data between communication protocols for retransmission. For example, the second communication module 54 receives transmissions from multiple physiological sensors 40 in tandem and the processor 55 executes a first module to convert the data from the sensors 40 from the Bluetooth® standard to a second standard using Wi-Fi technology for retransmission to the tablet 30. The tablet 30 may be located within the scan room 10, the control room 11, or in another location within range of the interface module 50. The processor 55 may also be executing a second module to convert the data from the sensors 40 to a computer networking standard, such as Ethernet, for retransmission via the network interface 56 to the controller 20 or another device connected to the LAN 60.

Referring to FIGS. 2-7, it is contemplated that the interface module 50 may be configured to execute with numerous configurations of physical networks. A first interface module 50 may be positioned within and manage communications with each of the wireless device within the scan room 10. A second interface module 50 may be positioned within and manage communications with each of the wireless device within the control room 11. The two interface modules 50 may be connected via the network 60 and a dedicated network cable 58, or wireless communications via a Wi-Fi standard. Optionally, a single interface module 50 may be positioned either within the scan room 10 or within the control room 11 and an antenna 70 positioned in the other room, connected via an antenna cable 72. Thus, a single wireless module 50 may be configured to receive and/or transmit wireless communications in both the scan room 10 and the control room 11. As still another option, an MRI compatible tablet 30 may be configured to execute as the interface module 50.

The quality of an MRI scans may be impacted by movement of the patient. Even when remaining "still," portions of the patient's anatomy, such as the heart and lungs, remain in motion. In order to improve image quality, the processor 55 on the interface module 50 may generate a gating signal to the PAC 45. The interface module 50 is in communication with the controller 20 and each of the physiological sensors 40. Consequently, the interface module 50 may receive a command from the controller 20 to begin a scan. The interface module 50 generates the gating signal as a function of the physiological data received from one or more of the sensors 40. The gating signal may initiate a magnetic pulse at the same phase of a heartbeat or respiration cycle, such that the patient's anatomy is in substantially the same physical location.

During an MRI scan, it may be desirable for an operator in the control room 11 to communicate with the patient in the scan room 10. Further, some scans take tens of minutes or up to an hour to perform. Thus, it may also be desirable for the operator to monitor the condition of the patient during the scan. A wireless headset 90 may be configured to communicate with the interface module 50. The MRI operator may talk into a microphone in the control room 11 and the communication transmitted to the wireless headset 90. The microphone may be a stand-alone unit connected, for example to the controller 20. Optionally, a tablet 30 may be located in the control room 11 and integrated microphone and speakers may be used by the operator to communicate with the patient. According to still another embodiment, the operator may have a wireless headset 90 with an integral microphone 96, configured to communicate with the patient's headset 90. Using the microphone, the MRI operator may provide audio instructions to the patient such as to hold their breath for a period of time. Similarly, a microphone 96 may be integral to the patient's headset 90 or otherwise provided to the patient such that the patient may similarly wirelessly communicate with the MRI operator, allowing two-way communication between the patient and the MRI operator.

Referring again to FIGS. 8 and 9, the wireless communication system may be configured to operate in cooperation with an existing, wired communication system. For example, an intercom system may provide a microphone for the technologist and a speaker 25 located in the scan room 10. A cable 21 may be provided to transmit the audio signal from the microphone to the speaker 25. The intercom system may further be integrated with the MRI controller 20 such that a single cable 21 extends from the controller 20 into the scan room 10. Due to the length of some scans, patients may be more at ease if some form of entertainment distracts them during the scan. The tablet 30 may store audio files, such as .mp3 or .wav files which may be streamed to the controller 20 as a supplemental audio source.

One or more interface modules 50 are provided to distribute the audio signals to the patient. The controller 20 may combine the audio signal from the tablet with the audio signal from the intercom and transmit both audio signals via the cable 21. If multiple interface modules 50 are configured to transmit the two audio signals, as shown in FIG. 9, one of the interface modules 50 is configured to first separate the two audio signals. Each of the audio signals is transmitted via the cable 21 to a second interface module 50. According to one embodiment of the invention, the cable 21 includes one or more conductors not used by the controller 20. The interface module 50 transmits the intercom audio signal via its normal signal wires and the secondary audio signal via one or more of the unused conductors. Optionally, an additional cable may be run between the two interface modules 50. According to yet another embodiment of the invention, the supplemental audio source may provide an audio signal directly to the interface module 50 for retransmission.

A second interface module 50 receives the two audio signals and passes the intercom signal through to the speaker 25 in the scan room. The second interface module 50 also converts at least one of the audio signals into a modulated RF signal. The interface module 50 may monitor the intercom signal to detect when the technologist is communicating with the patient. During periods of communication, the wireless communication module 52 may convert the intercom audio signal for transmission and during periods with no communication, the wireless communication module 52 may convert the second audio signal. Optionally, the wireless communication module 52 may continually convert both signals for transmission and superimpose the intercom signal over the audio signal. According to still another option, the wireless communication module 52 may continually convert the second audio signal and allow the intercom signal to be delivered via the speaker 25. If a single interface module 50 is configured to transmit the two audio signals, the combined audio signal may be transmit between the controller and the single interface module 50 as shown in FIG. 8, and the single interface module 50 further handles transmission of each of the audio signals into the scan room 10. It is further contemplated that a video signal may also be combined with the audio signals which is subsequently separated y the interface modules 50 and transmitted to a wireless video display module 80.

According to another embodiment of the invention, the operator may wish to provide information and/or instruction to the patient via visual information. For example, feedback from one or more of the physiological sensors may be displayed. Optionally, a visual representation of when to inhale and exhale such as a strip chart or a varying color indicator may be displayed on the display module 80 or wireless viewing device 110. Other visual stimuli may similarly be provided to the patient via either the display module 80 or wireless viewing device 110 to evaluate, for example, the patient's response to such stimuli.

During an MRI scan it is often desirable for the operator to receive other feedback from the patient. Although, the operator may be able to observe at least a portion of the patient via the window 15 between the scan room 10 and the control room 11, a significant portion of the patient may be within the bore of the scanner and out of view of the operator. A camera may be located in the scan room 10 and oriented to monitor the patient. The camera may provide a field of view, for example, within the bore 14 of the MRI scanner 12 that the operator may otherwise not be able to see. The images from the camera are wirelessly transmitted from the scan room 10 to the control room 11 via any of the embodiments of the communication system previously described so the operator may monitor the status of the patient during the MRI scan. Optionally, the patient may be provided with a handheld wireless feedback device from which the patient may be able to press one or buttons indicating a range of feelings from discomfort to an emergency situation. The wireless feedback device may also be used by the patient to provide feedback to stimuli during the scan. The handheld feedback device may be incorporated, for example, into a remote control used to control entertainment options as discussed below. The handheld feedback device similarly wirelessly transfers data from the scan room 10 to the control room 11 via any of the embodiments of the communication system previously described.

It is further contemplated that entertainment options may be provided to the patient during the scan. A display module 80 may be positioned such that the patient may view the monitor 82 during the course of the scan. According to one embodiment, the tablet 30 may be configured to be the display module 80 and the monitor on the tablet corresponds to the monitor 82 of the display module. According to yet another option, the video entertainment may be displayed on the wireless viewing device 110. The interface module 50 may receive a digital video and wirelessly communicate the video content to the monitor 82 and the audio content to the headset 90. Optionally, music may be wirelessly streamed to the headset 90. Similarly, access to the Internet may be provided on the monitor 82 via the wireless communication system. The patient may control the content displayed or heard via the microphone 96 and a voice recognition module executing on interface module 50 or a remote computer connected to the interface module 50. Optionally, a wireless remote control communicating, for example, via the Bluetooth® standard may be provided to the patient to control the audio and/or video content. It is further contemplated, that a tablet 30 in the scan room 10 and a tablet 30 in the control room 11 may facilitate direct audio and/or video communications between the patient and MRI operator utilizing integrated camera, microphones, and speakers within each tablet 30.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A communication system to permit communication between a patient undergoing a diagnostic imaging procedure in a scan room and a technologist in a control room conducting the diagnostic imaging procedure, wherein the diagnostic imaging equipment includes a scanner configured to generate a diagnostic image located in the scan room and a controller configured to control operation of the scanner located in the control room, the communication system comprising;
   an interface module operable to transfer an audio signal between the control room and the scan room, the interface module including:
      an input connection configured to receive the audio signal from the controller,
      a wireless communication module configured to convert the audio signal to a radio frequency (RE) modulated signal having a frequency greater than a frequency of operation of the diagnostic scanner, and
      an output connection configured to conduct the RF modulated signal;
   an antenna located in the scan room and electrically connected to the output connection of the interface module and configured to transmit the RF modulated signal in proximity to the scanner; and
   at least one wireless receiver configured to be positioned in proximity to the scanner and to receive the RF modulated signal.

2. The communication system of claim 1 further comprising a supplemental audio source supplying a second audio signal, wherein:
   the controller includes a logic circuit configured to combine the second audio signal with the audio signal from the controller to generate a combined audio signal,
   the combined audio signal is received at the input connection of the interface module, and
   the interface module further includes:
      an electronic circuit configured to separate the audio signal from the controller and the second audio signal out of the combined audio signal, and
      a second output connection configured to conduct the audio signal from the controller, wherein at least one of the audio signal from the controller and the second audio signal is converted to the RF modulated signal.

3. The communication system of claim 1 wherein the antenna is integrated in the interface module.

4. The communication system of claim 1 wherein the wireless receiver is a wireless headset.

5. The communication system of claim 1 further comprising:
   a supplemental audio source supplying a second audio signal, wherein the controller includes an electronic circuit configured to combine the second audio signal with the audio signal from the controller to generate a combined audio signal;
   a second interface module, including
      an input connection configured to receive the combined audio signal from the controller,
      an electronic circuit configured to separate the audio signal from the controller and the second audio signal out of the combined audio signal, and
      an output connection configured to receive a cable including multiple conductors; and
   the cable connected between the output connection of the second interface module and the input connection of the interface module, wherein:
   the audio signal from the controller and the second audio signal are transmitted on different conductors of the cable,
   the interface module further includes a second output connection configured to conduct the audio signal from the controller, and
   at least one of the audio signal from the controller and the second audio signal is converted to the RF modulated signal.

6. A communication system for radio frequency (RF) communications between a device within a shielded scan room housing a medical diagnostic scanner and a device external to the shielded scan room, wherein RF shielding exists around the shielded scan room, the communication system comprising:
   a first device operable to be located within the shielded scan room proximate to the medical diagnostic scanner and configured to transmit and receive at least one RF modulated signal;
   an interface module operable to communicate with the first device and to transfer a signal received from the first device within the shielded scan room to a second device external to the shielded scan room, the interface module including a wireless communication module configured to transmit and receive at least one RF modulated signal with the at least one device located within the shielded scan room, wherein the RF modulated signals have a frequency greater than a frequency of operation of the diagnostic scanner; and
   an antenna configured to exchange the RF modulated signals between the interface module and the first device.

7. The communication system of claim 6 wherein the first device is a sensor configured to monitor a physiological parameter of a patient in the medical diagnostic scanner and the at least one RF modulated signal transmitted from the first device includes data corresponding to the physiological parameter being monitored.

8. The communication system of claim 7 wherein the sensor includes an accelerometer generating a signal corresponding to motion of the sensor wherein the sensor is further configured to transmit the at least one RF modulated signal to the interface module further includes the signal from the accelerometer.

9. The communication system of claim 7 wherein the second device is a portable computing device having low magnetic susceptibility, the portable computing device including:
   a wireless communication module configured to receive the RF modulated signals from the sensor,
   a memory device configured to store the signals from the sensor, and
   a display configured to provide a visual indication of the signals from the sensor to an operator.

10. The communication system of claim 9 wherein the medical diagnostic scanner includes a physiological acquisition control (PAC) unit configured to control image acquisition on the medical diagnostic scanner via a gating signal and wherein the PAC unit is further configured to receive an RF modulated signal which includes the gating signal from the interface module.

11. The communication system of claim 10 wherein the portable computing device is further configured to execute a stored program to generate the gating signal for the PAC unit as a function of the signals received from the sensor and to transmit the gating signal to the PAC unit.

12. The communication system of claim 6, wherein the first device provides bidirectional communication with a patient in the medical diagnostic scanner.

13. A wireless communication system for use during a diagnostic imaging procedure to communicate between a control room, which includes a controller configured to control operation of a diagnostic scanner, and a shielded scan room which contains the diagnostic scanner, wherein RF shielding exists around the shielded scan room, the wireless communication system comprising:
   at least one portable device configured to engage a patient in the diagnostic scanner during operation of the diagnostic scanner, wherein the portable device includes a wireless communication module configured to transmit and receive radio frequency (RF) modulated signals, wherein the RF modulated signals have a frequency greater than a frequency of operation of the diagnostic scanner;
   a portable computing device including a memory device configured to store data and a series of instructions, a processor configured to execute the series of instructions, and a wireless communication module; and
   an interface module configured to transmit and receive RF modulated signals between the at least one portable device within the shielded scan room and with the portable computing device.

14. The wireless communication system of claim 13 wherein each of the portable devices are sensors configured to monitor a physiological parameter of the patient in the diagnostic scanner and to generate a signal corresponding to the physiological parameter being monitored and wherein each of the signals corresponding to the physiological parameter being monitored are converted to RF modulated signals and transmitted to the portable computing device via the interface module.

15. The wireless communication system of claim 14 wherein the diagnostic scanner further includes a physiological acquisition control (PAC) unit configured to control image acquisition on the diagnostic scanner via a gating signal and wherein the processor on the portable device is configured to:
   execute the series of instructions to generate the gating signal as a function of at least one of the RF modulated signals corresponding to the physiological parameter being received from the sensors,
   convert the gating signal to an RF modulated signal, and
   transmit the RF modulated signal corresponding to the gating signal to the PAC unit.

16. The wireless communication system of claim 13 wherein:
   the portable computing device is configured to retrieve a stored data file including one of stored audio data and stored video data and transmit the stored data file as an audio signal or a video signal, respectively, to the controller, and
   the controller includes a microphone configured to generate an audio signal and the controller is further configured to combine the audio signal or the video signal from the portable computing device with the audio signal from the microphone for transmission to the patient.

17. The wireless communication system of claim 16 wherein the interface module includes:
   an input connection configured to receive the combined signal from the controller,
   an electronic circuit configured to separate the audio or the video signal retrieved from the stored data file from the audio signal generated from the microphone,
   a wireless communication module configured to convert at least one of the audio or video signals to a radio frequency (RF) modulated signal having a frequency greater than a frequency of operation of the diagnostic scanner,
   an antenna configured to transmit the RF modulated signal in proximity to the scanner, and
   an output connection configured to conduct the audio signal generated from the microphone; and
   the wireless communication system further comprises at least one receiver configured to be positioned in proximity to the scanner and to receive the RF modulated signal.

18. The communication system of claim 17 wherein the wireless receiver is one of a wireless headset and a wireless monitor.

19. The communication system of claim 6 wherein one of the devices located within the scan room is a handheld feedback device configured to receive input from the patient.

20. The wireless communication system of claim 13 wherein the at least one portable device configured to engage the patient is a handheld feedback device configured to receive input from the patient.

* * * * *